(12) United States Patent
Hodges

(10) Patent No.: US 10,660,998 B2
(45) Date of Patent: May 26, 2020

(54) DEVICES AND METHODS FOR MONITORING BEARING AND SEAL PERFORMANCE

(71) Applicant: TC1 LLC, St. Paul, MN (US)

(72) Inventor: William V. Hodges, Tracy, CA (US)

(73) Assignee: TCI LLC, St. Paul, MN (US)

( * ) Notice: Subject to any disclaimer, the term of this patent is extended or adjusted under 35 U.S.C. 154(b) by 0 days.

(21) Appl. No.: 16/322,403

(22) PCT Filed: Aug. 10, 2017

(86) PCT No.: PCT/US2017/046244
§ 371 (c)(1),
(2) Date: Jan. 31, 2019

(87) PCT Pub. No.: WO2018/031741
PCT Pub. Date: Feb. 15, 2018

(65) Prior Publication Data
US 2019/0343998 A1    Nov. 14, 2019

Related U.S. Application Data

(60) Provisional application No. 62/374,726, filed on Aug. 12, 2016.

(51) Int. Cl.
*A61M 1/10* (2006.01)
*A61M 1/12* (2006.01)

(52) U.S. Cl.
CPC ........ *A61M 1/1025* (2014.02); *A61M 1/1013* (2014.02); *A61M 1/1031* (2014.02); *A61M 1/1086* (2013.01); *A61M 1/122* (2014.02)

(58) Field of Classification Search
None
See application file for complete search history.

(56) References Cited

U.S. PATENT DOCUMENTS 2,712,792 A    7/1955  Snyder
4,082,376 A    4/1978  Wehde et al.
(Continued)

FOREIGN PATENT DOCUMENTS

CA        2624704 A1    4/2007
CN      101282748 A    10/2008
(Continued)

OTHER PUBLICATIONS

International Search Report dated Nov. 22, 2017 for PCT/US2017/046244, 4 pages.

*Primary Examiner* — Brian T Gedeon
(74) *Attorney, Agent, or Firm* — Kilpatrick Townsend & Stockton LLP

(57) ABSTRACT

Blood pump devices having one or more sensors for monitoring performance of a bearing assembly and/or a fluid-tight seal are provided herein. Such devices are particularly useful in blood pump devices that have cantilevered rotors supported by a sealed mechanical bearing disposed outside a blood flow path of the device to avoid thrombus formation caused by blood contact with the bearing. The one or more sensors can include one or more accelerometers adapted to detect movement of the bearing assembly along one or more axes during operation of the pump. A vibration profile can be determined from the movement data from the one or more sensors that is indicative of performance of the bearing assembly and/or seal so as to allow monitoring over time.

24 Claims, 8 Drawing Sheets

(56) References Cited

U.S. PATENT DOCUMENTS

| | | |
|---|---|---|
| 4,458,366 A | 7/1984 | MacGregor |
| 4,508,535 A | 4/1985 | Joh et al. |
| 4,625,712 A | 12/1986 | Wampler |
| 4,688,998 A | 8/1987 | Olsen et al. |
| 4,704,121 A | 11/1987 | Moise |
| 4,779,614 A | 10/1988 | Moise |
| 4,817,586 A | 4/1989 | Wampler |
| 4,846,152 A | 7/1989 | Wampler et al. |
| 4,895,557 A | 1/1990 | Moise et al. |
| 4,906,229 A | 3/1990 | Wampler |
| 4,908,012 A | 3/1990 | Moise et al. |
| 4,944,722 A | 7/1990 | Carriker et al. |
| 4,957,504 A | 9/1990 | Chardack |
| 4,994,078 A | 2/1991 | Jarvik |
| 5,098,256 A | 3/1992 | Smith |
| 5,106,273 A | 4/1992 | Lemarquand et al. |
| 5,376,114 A | 12/1994 | Jarvik |
| 5,385,581 A | 1/1995 | Bramm et al. |
| 5,393,207 A | 2/1995 | Maher et al. |
| 5,405,251 A | 4/1995 | Sipin |
| 5,441,535 A | 8/1995 | Takahashi et al. |
| 5,443,503 A | 8/1995 | Yamane |
| 5,588,812 A | 12/1996 | Taylor et al. |
| 5,613,935 A | 3/1997 | Jarvik |
| 5,695,471 A | 12/1997 | Wampler |
| 5,707,218 A | 1/1998 | Maher et al. |
| 5,711,753 A | 1/1998 | Pacella et al. |
| 5,749,855 A | 5/1998 | Reitan |
| 5,755,784 A | 5/1998 | Jarvik |
| 5,824,070 A | 10/1998 | Jarvik |
| 5,888,242 A | 3/1999 | Antaki et al. |
| 5,904,646 A | 5/1999 | Jarvik |
| 5,917,297 A | 6/1999 | Gerster et al. |
| 5,928,131 A | 7/1999 | Prem |
| 5,947,892 A | 9/1999 | Benkowski et al. |
| 5,951,263 A | 9/1999 | Taylor et al. |
| 5,957,672 A | 9/1999 | Aber |
| 6,001,056 A | 12/1999 | Jassawalla et al. |
| 6,018,208 A | 1/2000 | Maher et al. |
| 6,050,975 A | 4/2000 | Poirier |
| 6,066,086 A | 5/2000 | Antaki et al. |
| 6,071,093 A | 6/2000 | Hart |
| 6,093,001 A | 7/2000 | Burgreen et al. |
| 6,116,862 A | 9/2000 | Rau et al. |
| 6,123,659 A | 9/2000 | le Blanc et al. |
| 6,135,710 A | 10/2000 | Araki et al. |
| 6,146,325 A | 11/2000 | Lewis et al. |
| 6,149,683 A | 11/2000 | Lancisi et al. |
| 6,186,665 B1 | 2/2001 | Maher et al. |
| 6,227,797 B1 | 5/2001 | Watterson et al. |
| 6,227,820 B1 | 5/2001 | Jarvik |
| 6,234,772 B1 | 5/2001 | Wampler et al. |
| 6,254,359 B1 | 7/2001 | Aber |
| 6,264,635 B1 | 7/2001 | Wampler et al. |
| 6,278,251 B1 | 8/2001 | Schob |
| 6,293,901 B1 | 9/2001 | Prem |
| 6,394,769 B1 | 5/2002 | Bearnson et al. |
| 6,447,266 B2 | 9/2002 | Antaki et al. |
| 6,623,475 B1 | 9/2003 | Siess |
| 6,688,861 B2 | 2/2004 | Wampler |
| 6,692,318 B2 | 2/2004 | McBride |
| 6,942,611 B2 | 9/2005 | Siess |
| 6,991,595 B2 | 1/2006 | Burke et al. |
| 7,011,620 B1 | 3/2006 | Siess |
| 7,070,398 B2 | 7/2006 | Olsen et al. |
| 7,229,258 B2 | 6/2007 | Wood et al. |
| 7,303,553 B2 | 12/2007 | Ott |
| 7,338,521 B2 | 3/2008 | Antaki et al. |
| 7,563,225 B2 | 7/2009 | Sugiura |
| 7,575,423 B2 | 8/2009 | Wampler |
| 7,578,782 B2 | 8/2009 | Miles et al. |
| 7,682,301 B2 | 3/2010 | Wampler et al. |
| 7,699,586 B2 | 4/2010 | LaRose et al. |
| 7,699,588 B2 | 4/2010 | Mendler |
| 7,753,645 B2 | 7/2010 | Wampler et al. |
| 7,798,952 B2 | 9/2010 | Tansley et al. |
| 7,802,966 B2 | 9/2010 | Wampler et al. |
| 7,824,358 B2 | 11/2010 | Cotter et al. |
| 7,841,976 B2 | 11/2010 | McBride et al. |
| 7,850,594 B2 | 12/2010 | Sutton et al. |
| 7,861,582 B2 | 1/2011 | Miyakoshi et al. |
| 7,862,501 B2 | 1/2011 | Woodard |
| 7,927,068 B2 | 4/2011 | McBride et al. |
| 7,959,551 B2 | 6/2011 | Jarvik |
| 7,963,905 B2 | 6/2011 | Salmonsen et al. |
| 7,976,271 B2 | 7/2011 | LaRose et al. |
| 7,988,728 B2 | 8/2011 | Ayre |
| 7,993,260 B2 | 8/2011 | Bolling |
| 7,997,854 B2 | 8/2011 | LaRose et al. |
| 8,002,518 B2 | 8/2011 | Woodard et al. |
| 8,007,254 B2 | 8/2011 | LaRose et al. |
| 8,096,935 B2 | 1/2012 | Sutton et al. |
| 8,118,723 B2 | 2/2012 | Richardson et al. |
| 8,118,724 B2 | 2/2012 | Wampler et al. |
| 8,152,493 B2 | 4/2012 | LaRose et al. |
| 8,152,845 B2 | 4/2012 | Bourque |
| 8,177,703 B2 | 5/2012 | Smith et al. |
| 8,282,359 B2 | 10/2012 | Ayre et al. |
| 8,323,174 B2 | 12/2012 | Jeevanandam et al. |
| 8,343,028 B2 | 1/2013 | Gregoric et al. |
| 8,353,686 B2 | 1/2013 | Cook |
| 8,366,381 B2 | 2/2013 | Woodard et al. |
| 8,366,599 B2 | 2/2013 | Tansley et al. |
| 8,376,707 B2 | 2/2013 | McBride et al. |
| 8,449,444 B2 | 5/2013 | Poirier |
| 8,506,471 B2 | 8/2013 | Bourque |
| 8,562,508 B2 | 10/2013 | Dague et al. |
| 8,597,350 B2 | 12/2013 | Rudser et al. |
| 8,652,024 B1 | 2/2014 | Yanai et al. |
| 8,657,733 B2 | 2/2014 | Ayre et al. |
| 8,668,473 B2 | 3/2014 | LaRose et al. |
| 8,864,643 B2 | 10/2014 | Reichenbach et al. |
| 9,265,870 B2 | 2/2016 | Reichenbach et al. |
| 9,533,082 B2 | 1/2017 | Reichenbach et al. |
| 9,717,832 B2 | 8/2017 | Taskin et al. |
| 9,717,833 B2 | 8/2017 | Mcbride et al. |
| 10,029,038 B2 | 7/2018 | Hodges |
| 2002/0147495 A1 | 10/2002 | Petroff |
| 2002/0149200 A1 | 10/2002 | Fumioka |
| 2003/0068227 A1 | 4/2003 | Yamazaki |
| 2003/0100816 A1 | 5/2003 | Siess |
| 2003/0135086 A1 | 7/2003 | Khaw et al. |
| 2004/0236420 A1 | 11/2004 | Yamane et al. |
| 2005/0004421 A1 | 1/2005 | Pacella et al. |
| 2005/0071001 A1 | 3/2005 | Jarvik |
| 2005/0095151 A1 | 5/2005 | Wampler et al. |
| 2005/0107657 A1 | 5/2005 | Carrier et al. |
| 2005/0147512 A1 | 7/2005 | Chen et al. |
| 2005/0254976 A1 | 11/2005 | Carrier et al. |
| 2007/0078293 A1 | 4/2007 | Shambaugh, Jr. et al. |
| 2007/0100196 A1 | 5/2007 | Larose et al. |
| 2007/0156006 A1 | 7/2007 | Smith et al. |
| 2008/0021394 A1 | 1/2008 | LaRose et al. |
| 2008/0269880 A1 | 10/2008 | Jarvik |
| 2009/0118567 A1 | 5/2009 | Siess |
| 2009/0203957 A1 | 8/2009 | LaRose et al. |
| 2010/0069847 A1 | 3/2010 | LaRose et al. |
| 2010/0145133 A1 | 6/2010 | Bolling et al. |
| 2010/0150749 A1 | 6/2010 | Horvath |
| 2010/0152526 A1 | 6/2010 | Pacella et al. |
| 2011/0054239 A1 | 3/2011 | Sutton et al. |
| 2011/0118998 A1 | 5/2011 | Loose et al. |
| 2011/0144413 A1 | 6/2011 | Foster |
| 2011/0152600 A1 | 6/2011 | Scott et al. |
| 2011/0237863 A1 | 9/2011 | Ricci et al. |
| 2011/0245582 A1 | 10/2011 | Zafirelis et al. |
| 2012/0035411 A1 | 2/2012 | LaRose et al. |
| 2012/0046514 A1 | 2/2012 | Bourque |
| 2012/0095281 A1 | 4/2012 | Reichenbach et al. |
| 2012/0134793 A1 | 5/2012 | Wu et al. |
| 2012/0134832 A1 | 5/2012 | Wu |
| 2012/0172655 A1 | 7/2012 | Campbell et al. |
| 2012/0253103 A1 | 10/2012 | Robert |
| 2012/0310036 A1 | 12/2012 | Peters et al. |

(56) References Cited

U.S. PATENT DOCUMENTS

| | | |
|---|---|---|
| 2013/0096364 A1 | 4/2013 | Reichenbach et al. |
| 2013/0121821 A1 | 5/2013 | Ozaki et al. |
| 2013/0127253 A1 | 5/2013 | Stark et al. |
| 2013/0170970 A1 | 7/2013 | Ozaki et al. |
| 2013/0225909 A1 | 8/2013 | Dormanen et al. |
| 2013/0314047 A1 | 11/2013 | Eagle et al. |
| 2014/0296615 A1 | 10/2014 | Franano |
| 2014/0324165 A1 | 10/2014 | Burke |
| 2015/0005572 A1 | 1/2015 | Reichenbach et al. |
| 2015/0285258 A1 | 10/2015 | Foster |
| 2016/0074574 A1 | 3/2016 | Welsch et al. |
| 2016/0144089 A1 | 5/2016 | Woo et al. |
| 2016/0369814 A1 | 12/2016 | Schibli et al. |
| 2017/0021069 A1 | 1/2017 | Hodges |

FOREIGN PATENT DOCUMENTS

| | | |
|---|---|---|
| DE | 19854724 A1 | 5/1999 |
| DE | 102009047844 A1 | 3/2011 |
| EP | 0 150 320 B1 | 5/1990 |
| EP | 0 583 781 A1 | 2/1994 |
| JP | 2009511802 A | 3/2009 |
| KR | 20080056754 A | 6/2008 |
| WO | 0043054 A2 | 7/2000 |
| WO | 2007040663 A1 | 4/2007 |
| WO | 2008152425 A1 | 12/2008 |

DEVICES AND METHODS FOR MONITORING BEARING AND SEAL PERFORMANCE

CROSS-REFERENCES TO RELATED APPLICATIONS

This application claims the benefit of U.S. Provisional Application No. 62/374,726 filed Aug. 12, 2016, the entire contents of which are incorporated herein by reference.

This application relates generally to U.S. application Ser. No. 15/216,528 filed Jul. 21, 2016, entitled "Cantilevered Rotor Pump and Methods for Axial Flow Blood Pumping"; U.S. Application No. 62/365,305 filed Jul. 21, 2016, entitled "Rotary Seal for Cantilevered Rotor Pump and Methods for Axial Flow Blood Pumping"; U.S. application Ser. No. 14/489,041 filed Sep. 17, 2014, entitled "Pump and Method for Mixed Flow Blood Pumping"; and U.S. application Ser. No. 13/273,185 filed Oct. 13, 2011, entitled "Pumping Blood" (now U.S. Pat. No. 9,265,870); each of which is incorporated herein by reference in its entirety for all purposes.

BACKGROUND

This application relates generally to mechanical circulatory support systems, and more specifically relates to improved rotor designs in axial flow blood pumps.

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

While blood pumps have been effective for many patients, because patients using such devices are living longer, further improvements that prolong the effectiveness and lifetime of such blood pump devices are desired. One challenge frequently encountered in axial blood pumps is that performance of the rotor, the bearing assembly or associated seal can degrade over time. Thus, there is a need for the ability to monitor and assess the performance of the pump over the lifetime of the device.

There are various conventional methodologies used for characterizing the normal operating conditions, wear, and the life of mechanical rotating assemblies. Some conventional techniques include vibration analysis, oil analysis, and ultrasound techniques. Since blood pumps are implanted devices, servicing the blood pump is not feasible. Further, commonly used conventional types of analysis used to monitor rotating machinery are not possible (e.g., oil analysis or attaching devices externally to characterize vibration). Thus, there is a need for improved blood pump designs that allow for monitoring of bearing performance and seal performance over the lifetime of the device in a non-invasive manner.

BRIEF SUMMARY

An axial flow mechanical circulatory support system having an improved rotor design with a sealed bearing assembly and one or more sensors to allow monitoring of the bearing assembly and seal is provided herein.

In one aspect, the invention provides an implantable blood pump having a rotor supported by a sealed bearing assembly and having one or more sensors adapted to detect movement of the bearing assembly. An output from the sensors can be used to determine and monitor performance of the bearing assembly and/or seal over time. The bearing assembly can be a mechanical bearing assembly or any other type of bearing assembly, such as any of those described herein.

In some embodiments, the blood pump includes a pump housing defining a blood flow passage therethrough, a rotor, a mechanical bearing assembly with a seal, and one or more sensors. The rotor includes a rotatable shaft that extends into the passage such that a distal portion of the rotor facilitates blood flow through the passage upon rotation of the shaft. The mechanical bearing assembly is coupled with a proximal portion of the rotatable shaft to allow rotation of the rotor during operation of the pump. The seal is disposed along the rotor shaft between the bearing assembly and the shaft and is adapted to inhibit contact between the bearing assembly and any blood flowing through the blood flow passage during operation of the pump. The one or more sensors are adapted and positioned to obtain movement data along one or more axes during operation of the pump for determination of performance of the bearing assembly and/or seal. This can be done either independently or by comparing the sensor output to a signature profile of the pump determined from prior movement data. In some embodiments, the one or more sensors are one or more accelerometers and can include single-axis accelerometers or at least one multi-axis accelerometer. The one or more sensors can also be acoustic emission sensors, optical detectors, proximity sensors, or any sensor suitable for detecting movements of the pump. Movement data can include movement of the bearing assembly (e.g. the entire bearing assembly or any individual component) and/or movement of the rotor shaft. In some aspects, movement data can include vibrations, such as cyclical vibrations, that is indicative of performance of the bearing assembly and/or the seal. Such indications of performance can be determined by independent analysis of the vibration data (e.g. vibration profile) or can be determined, at least in part, by comparing to a signature vibration profile of that type of pump or that particular pump.

In some embodiments, the one or more sensors include at least a first and second accelerometers adapted and positioned to detect movement data along first and second axes, respectively, the first and second axes being transverse to one another. The one or more sensors can also be acoustic emission sensors, optical detectors, proximity sensors, or any sensor suitable for detecting movements of the pump. The accelerometers can be secured within the pump housing, such as the aft cover and/or housing adjacent the side of the bearing assembly.

In some embodiments, the pump system includes a memory communicatively coupled with the one or more sensors that stores movement data obtained from the one or more sensors. The sensor output can then be collected periodically, or as needed. The system further includes a controller communicatively coupled with the one or more sensors that is configured to obtain movement data upon regular intervals, upon detection of a particular movement, and/or upon receiving a command to obtain data. The controller and one or more sensors can communicate either wirelessly or through a cabled connection. In some embodiments, the one or more sensors automatically store information on a memory and the controller obtains the recorded information at regular intervals, in response to detection of a particular movement or event, and/or upon receiving a command from a physician during a periodic checkup or performance assessment. In some embodiments, this is accomplished by the controller sending a command to the one or more sensors to obtain, store and/or transmit the information. In some embodiments, the one or more sensors include a microprocessor, ASIC, FPGA, and the like, which enables the sensor to automatically obtain and stored the information and/or to send a command to the controller, which can allow for additional information being monitored in response to a detected event (e.g. vibrational anomaly) or to allow feedback control of the pump based, at least in part, on information received from the sensors. In some embodiments, the system is configured with a combination analysis at the controller and sensor (e.g. the controller periodically sends a command signal to the sensor and the sensor returns data in response if a pre-determined condition has been met, otherwise returns null).

In some embodiments, the blood pump further includes a processor configured to determine a vibration profile from the movement data obtained from the one or more sensors, the vibration profile indicative of a performance of the bearing assembly and/or the seal. The vibration profile can be compared to a previously obtained vibration profile and/or a signature profile characteristic of the pump or a type of the pump. The processor can be configured to output the movement data or associated vibration profile to an external memory to be access by a physician or medical facility associated with the patient. The processor can also be configured to output the data or a notification to the treating physician if a determined vibration profile exceeds allowable performance parameters.

Methods of monitoring bearing and/or seal performance in a blood pump are also provided. Such methods can include: operating a blood pump so as to transport blood along a blood flow path through a pump housing of the blood flow pump and obtaining movement data from one or more sensors coupled with the pump. Typically, the movement data is indicative of movement of the bearing assembly along one or more axes during operation of the pump. In some embodiments, operating the blood pump can include rotating a shaft of the rotor so that movement of the rotor forces blood along the blood flow path. The rotor can be rotatably supported by a bearing assembly that is sealed from blood flowing through the blood flow path by a rotary seal. Such methods can further include: determining a vibration profile of the pump from the movement data from the one or more sensors from which a performance of the bearing assembly and/or the rotary seal can be determined.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim. The invention will be better understood upon reading the following description and examining the figures which accompany it.

BRIEF DESCRIPTION OF THE DRAWINGS

Further details, aspects, and embodiments of the invention will be described by way of example only and with reference to the drawings. In the drawings, like reference numbers are used to identify like or functionally similar elements. Elements in the figures are illustrated for simplicity and clarity and have not necessarily been drawn to scale.

DETAILED DESCRIPTION

Figure 1:
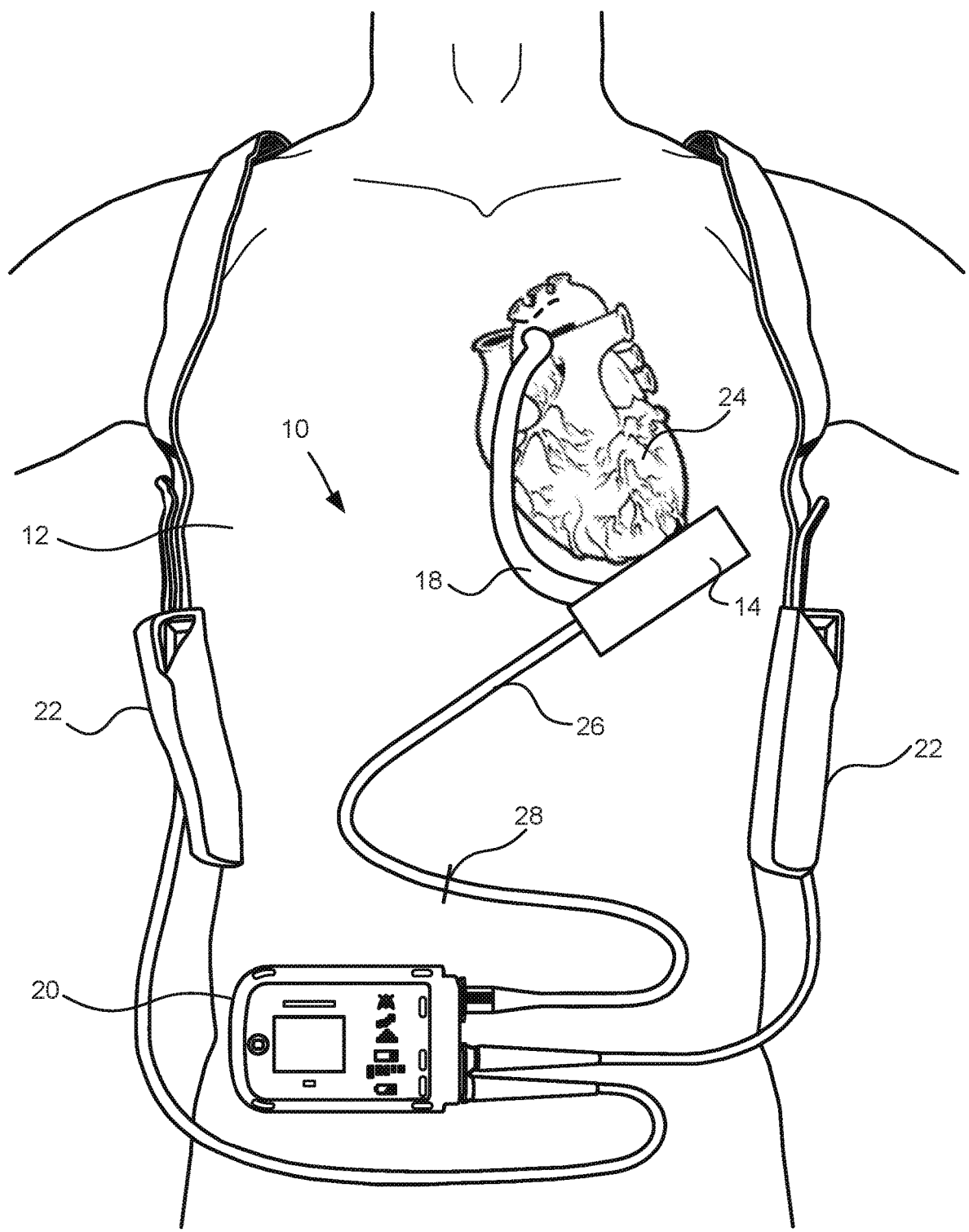
FIG. 1 is an illustration of a mechanical circulatory support system implanted in a patient's body in accordance with embodiments of the invention.

The above described systems and methods for monitoring bearing and seal performance are useful in an implanted blood pump, such as that shown in FIG. 1, particularly blood pumps having a cantilevered rotor design, such as those depicted in FIGS. 3-7, which can experience greater cyclical stresses within the bearing assembly due to the cantilevered design. It is appreciated that the devices and methods for monitoring bearing and seal performance described herein could be applied to any type of implantable pump or non-implantable pumps, in various applications, both medical and non-medical.

This invention pertains to monitoring a system vibration associated with the mechanical bearing assembly and/or seals used in an implantable blood pump, and particularly blood pumps having a cantilevered rotor design. In various embodiments, monitoring is performed by use of one or more sensors incorporated into the blood pump. Sensors, such as accelerometers or like sensors, can be mounted in one or more axis of the rotating assembly of the blood pump. Vibration can be used to characterize the normal operating conditions, wear, and the life of bearings and seals. This technique can also be used in the manufacturing of the pump to ensure that the components were correctly assembled and operate per specification. In some embodiments, acoustic emission sensors can be used to characterize the noise of a mechanical system. Noise signatures can also be developed to characterize wear and life of mechanical systems.

In one aspect, this approach can be used during manufacturing of the pump device to determine whether the device is operating properly and within suitable operating parameters, for example to assess rotor performance within the pump. This aspect is particularly useful in manufacturing of a cantilevered rotor design where the bearing assembly may be subjected to increased stresses as compared to conventional rotor redesign in implantable blood pumps.

In another aspect, this approach can be used as a diagnostic tool to assess changes in performance of the pump over time, which may be attributable to changes in the pump (e.g. degradation of the bearing assembly) or changes in a condition in the patient (e.g. blood viscosity, further degradation of heart performance). In some embodiments, the seal performance can be determined from the vibration signature. For example, if the seal is compromised and blood contacts the bearing assembly, formation of thrombus can adversely affect performance of the bearing assembly and rotor in a manner that is recognizable from the vibration signature.

In some embodiments, the blood pump system includes a memory that stores data associated with the sensor readings. The memory can be included in the implantable blood pump or within an associated controller device operatively coupled with the blood pump device. In some embodiments, the blood pump system includes a wireless communication device that periodically or continuously communicates sensor data to an external device for storage and/or analysis. Such embodiments can utilize a personal computing device (e.g. smartphone) of the user or any suitable data means to relay, store and process sensor data as would be understood by one of skill in the art. The sensor data can be processed to determine a vibration profile which can then be stored for subsequent retrieval by a physician and/or medical professional or can be automatically uploaded to an information system associated with a physician or medical facility associated with the patient. This approach allows the treating physician to readily recognize any change in performance based on the vibration signature, even remotely.

In another aspect, the sensor readings can be communicated to the controller of the blood pump and operation of the blood pump can be modified in response to the sensor readings. In some embodiments, the controller can determine a vibration signature profile from the sensors readings and modify a control parameter of the blood pump based on the vibration signature. For example, if the vibration signature profile is indicative of an unacceptable performance characteristic, then the pump can be slowed or varied in order to mitigate that performance characteristic.

In another aspect, the sensor readings can be obtained by the pump system at certain intervals (e.g. once a day, twice a day) in order to conserve power required to obtain, store and communicate sensor data. This approach is useful as the vibration signature often does not vary considerably during the course of one day, but rather tends to change gradually over a longer period of time (e.g. days, weeks, months) such that any performance issues can be recognized and dealt with before any problems occur.

Figure 3:
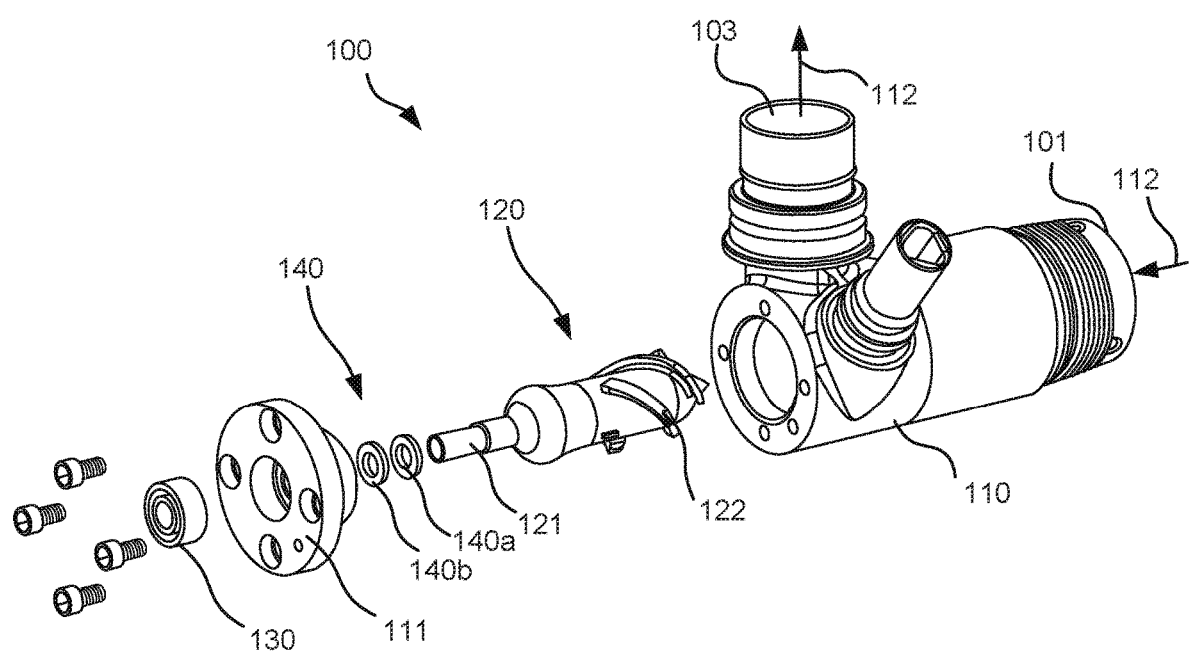
FIG. 3 shows an axial flow blood pump device with an improved rotor design in accordance with some embodiments.

Examples of pump configurations in which this approach can be used are illustrated in FIGS. 1 and 3. Examples of pump systems adapted with sensors for monitoring bearing and seal performance are depicted in FIGS. 4-7.

FIG. 1 is an illustration of a mechanical circulatory support system 10 implanted in a patient's body 12. The mechanical circulatory support system 10 include an implantable blood pump 14, outflow cannula 18, system controller 20, and power sources 22. The implantable blood pump 14 may include a VAD that is attached to an apex of the left ventricle, as illustrated, or the right ventricle, or both ventricles of the heart 24. The VAD is typically an axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. The blood pump 14 may be attached to the heart 24 via a ventricular cuff which is sewn to the heart 24 and coupled to the blood pump 14. The other end of the blood pump 14 connects to the ascending aorta via the outflow cannula 18 so that the VAD effectively diverts blood from the weakened ventricle and propels blood to the aorta for circulation to the rest of the patient's vascular system.

FIG. 1 illustrates the mechanical circulatory support system 10 during battery 22 powered operation. A driveline 26 which exits through an exit site 28 in the patient's abdomen, connects the implanted blood pump 14 to the system controller 20, which monitors system 10 operation. Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. The system may be powered by either one, two, or more batteries 22. It will be appreciated that although the system controller 20 and power source 22 are illustrated outside/external to the patient body, the driveline 26, system controller 20 and/or power source 22 may be partially or fully implantable within the patient, as separate components or integrated with the blood pump 14. Examples of such modifications are further described in U.S. Pat. No. 8,562,508 and U.S. Patent Publication No. 2013/0127253, each of which is incorporated herein by reference in its entirety for all purposes.

In some conventional blood pumps, the rotor is suspended by bearing assemblies near opposite ends of the rotor with the rotor blades between. The bearings are disposed within the blood flow path and lubricated, in part, by blood flowing across the bearings. Such bearings are known as bloodwashed bearings.

Figure 2:
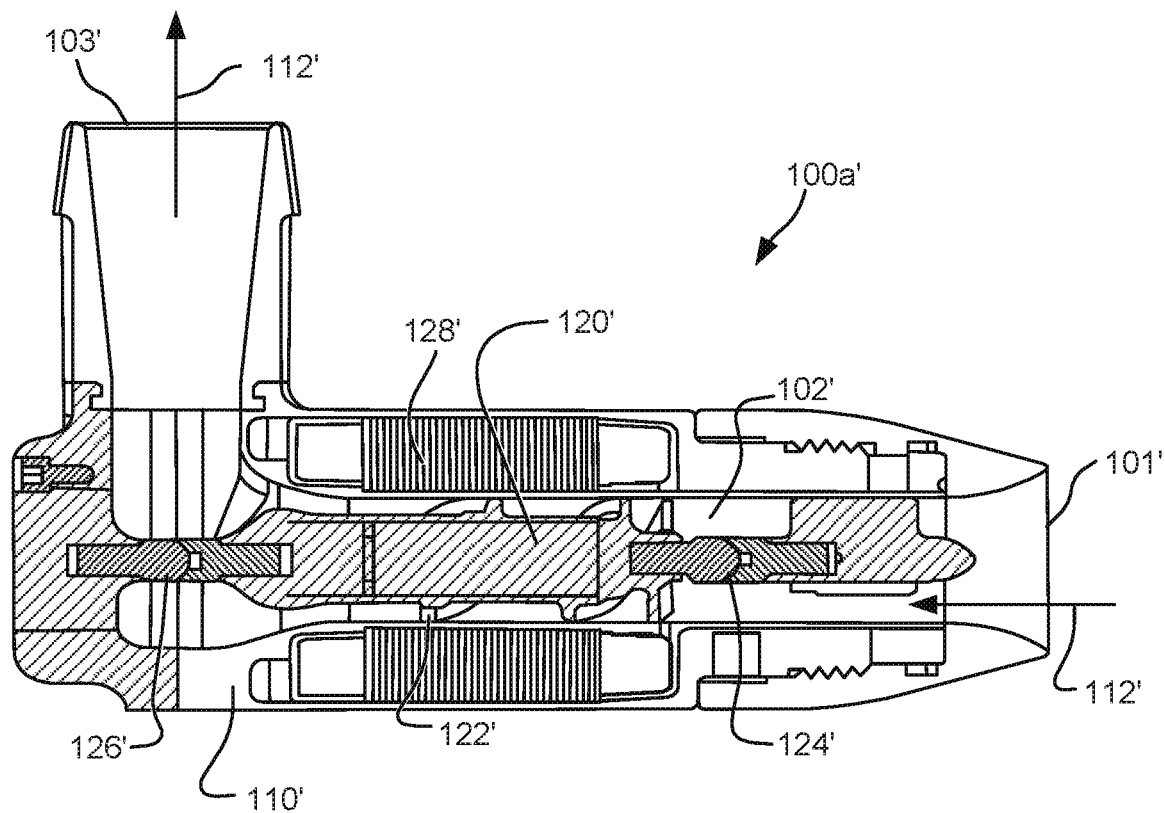
FIG. 2 shows a conventional axial blood flow pump device.

An example of such bearings can be understood by referring to FIG. 2, which shows a conventional axial flow blood pump 100'. The pump includes a housing 110' that defines a blood flow path 112'. Blood enters the housing 110' through an inlet 101', passes through a central tubular region 102' of the housing 110', and exits through an outlet 103'. The housing 110' contains a motor stator 128', which drives rotation of a rotor 120' located in the blood flow path 112'. As the rotor 120' rotates, blades 122' on the rotor 120' impart energy to the blood flow, resulting in pressure and blood flow at the outlet 103'. The rotor 120' is suspended in the housing 110' by fore and aft mechanical, blood-immersed bearings 124', 126' that limit axial translation of the rotor 120'. The bearings 124, 126 also limit the rotor from shifting off its axis of rotation and resist various destabilizing forces that occur during operation.

Studies have revealed that blood-washed bearings tend to develop thrombus over-time at the point of contact between the bearing ball and the cup in which the ball resides. Development of thrombus in the bearings can significantly degrade performance of the pump over time. In twelve chronic in-vivo animal studies, upon completion of the studies, the pumps were explanted and disassembled, after which it was observed that, in 50% of the pumps, either one or both bearings had some level of thrombosis evident.

To address these issues, recent developments include replacing blood washed mechanical bearings in rotary blood pumps that are used to suspend rotors with actively/passively magnetically suspended rotors. This allows for the removal of mechanical bearings in pumps, however, the magnetic levitation of the rotor creates hydrodynamic bearings between the pump housing and rotor. In addition, adding magnetics to VAD's significantly increases the complexity of the design and its operation since the magnets must generally maintain a radial position within the blood flow path as well as a longitudinal position. Due in part to these complexities, current versions of hydrodynamic bearings used in VAD's may still develop thrombus issues. In such designs, it is particularly useful to monitor the performance of the bearing assembly and the seal as described herein.

FIG. 3 illustrates an exploded view of an embodiment of an axial blood flow pump design with an improved cantilevered rotor design supported by a sealed bearing assembly having a rotary seal. The improved axial flow blood pump 100 includes a housing 110 that defines a blood flow path 112 that enters the housing 110 through an inlet 101, passes through a central tubular region of the housing and exits through an outlet 103. Housing 110 may be non-magnetic and may be made of a biocompatible material such as titanium or a suitable ceramic material which is non-thrombogenic, rigid, and exhibits minimum eddy current losses. Housing 110 contains a rotating means, such as a motor stator, adapted to drive rotation of rotor 120. Rotor 120 includes one or more rotor blades 122, typically a group of helical blades, on a distal portion that extends into the blood flow path 112. As rotor 120 rotates, rotor blades 122 impart energy to the blood flow, resulting in pressure and blood flow at the outlet 103. Rotor 120 is suspended in the housing 110 by a mechanical bearing assembly 130 disposed on a proximal portion of rotor 120 that extends through a hole in the rear cover 111 outside the blood flow path.

In some embodiments, rotor 120 is redesigned such that a circular rotor shaft 121 that extends proximally from the rear of the rotor and outside the blood flow path. Such a configuration allows for use of a traditional mechanical bearing (not blood or saline washed). Mechanical bearing 130 can be assembled within the rear cover 111 of the pump housing 110 such that any contact with the blood flow stream is avoided. In this embodiment, the shaft of rotor 120 slides through back cover 111 and can be press fit into the bearing assembly. At the shaft to plug interface, a mechanical rotary seal can be used to further ensure blood contact is avoided. A design of this nature reduces the static to dynamic interfaces from two to one. Furthermore, unlike blood washed bearings, this design does not rely on blood as a lubricant. Rotary seal keeps the blood from being used as a lubricant, which allows blood to be eliminated as a lubricant within rotary type blood pump devices. Since a sealed mechanical bearing assembly is used, this allows for a bearing design that utilizes various other types of lubricant (e.g. oil-based, silicone) and could use and/or adapt common bearings and lubricants from the mechanical arts as would be understood by one of skill from the description herein. Such mechanical bearings may provide improved performance and durability and increased life-times as compared to saline purged or blood washed designs.

Figure 4:
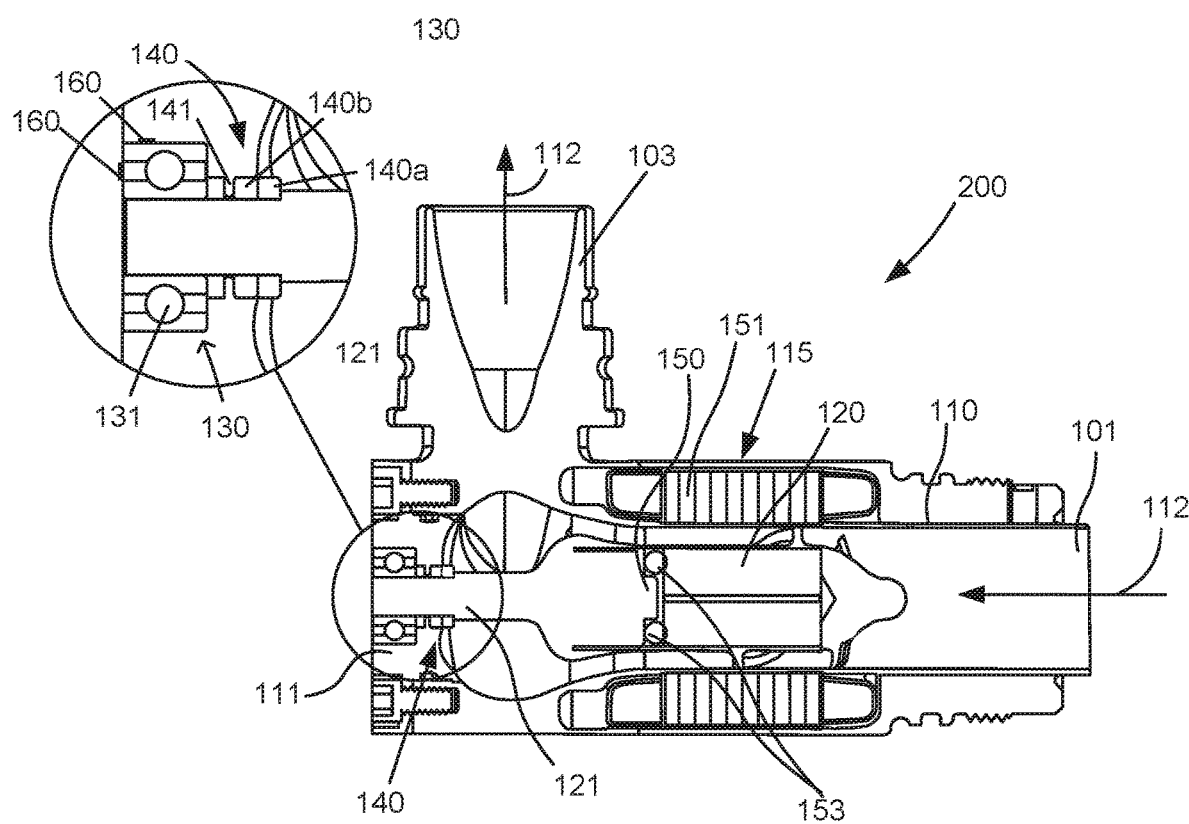
FIG. 4 shows another axial flow blood pump device with performance monitoring sensors in accordance with some embodiments.

Since mechanical bearing 130 couples the rotor at only one end, it provides cantilevered support and withstands lateral deflection of the rotor by applying a torque through the proximal portion. In some embodiments, the mechanical bearing may be selected to have an axial thickness extending along an axis of the rotor shaft between 0.050" to 0.500" to allow the bearing to withstand greater deflecting forces and apply greater reactive torques. In some embodiments, the device may include a mechanical bearing 130 consisting of multiple stacked radial bearing, such as two stacked radial bearings, as shown in FIG. 4. In another aspect, rotor 120 includes a fluid-tight seal 140 disposed between a proximal portion of the rotor coupled with mechanical bearing assembly 130 and a distal portion from which the rotor blades extend within the blood flow path.

As shown in FIG. 3, the rotary seal 140 includes two interfacing components, first seal face component 140a that is secured to the rotor shaft and revolves with the shaft and second seal face component 140b that remains secured with rear cover 111. Each of seal face is circular in shape with a central opening through which the rotor shaft extends and includes a flat surface that engages against a corresponding flat surface of the other seal face to provide a fluid-tight seal and inhibit blood flow into the bearing assembly while allowing rotation of the rotor shaft within the bearing assembly. One or both of the first and second components 140a, 140b can be formed of a hard and/or rigid material, such as silicon carbide, carbon/tungsten, ceramic, or any alloy or material suitable for withstanding the heat and variable forces that may occur during operation and maintaining a fluid-tight seal over the lifetime of the device. Also, one or both of the seals configured with a preload to allow the seals to track on one another while maintaining a sufficient seal.

It is particularly useful in such designs to monitor performance of the bearing assembly and rotary seal over time, such as described herein. It is appreciated that this monitoring approach is not limited to use with axial flow pumps, or even blood pumps, and could be used in various implantable or non-implantable pump devices, or any field there is a need for a robust monitoring of a mechanical bearing assembly and a seal that is liquid tight to ensure acceptable performance over a long period of time. Examples of such performance monitoring as used with blood pumps having a cantilevered rotor design are detailed further in the following embodiments.

FIG. 4 shows another exemplary pump 200 having a cantilevered rotor 120 in which the supporting mechanical bearing 130 is disposed outside the blood flow path, rotary seal 140 disposed between the blood flow path and bearing assembly 130 and sensors 160 for monitoring performance of the bearing assembly and/or seal. Each sensor 160 is an accelerometer. In this embodiment two sensors 160 are used so as to detect vibrational movement along at least two different axes, preferably first and second axes that are transverse or perpendicular. This allows an vibration signature derived from the sensor readings to account for vibrational movement in any direction. It is appreciated that a single sensor could be used, for example a multi-axis accelerometer. While in this embodiment the sensors 160 are coupled within the pump housing in contact or in close proximity to bearing assembly 130, it is appreciated that sensors 160 could be disposed anywhere on the pump so long as the sensor could still detect movement/vibrations from the bearing assembly during rotation of the rotor. Since such movements and vibrations could be attenuated as the vibrations travel through the pump housing and various other components, it is preferable that the sensors be fixedly coupled to the pump in close proximity to the bearing assembly.

In this embodiment, rotary seal 140 includes two interfacing seals, rotating face seal 140a attached to rotor shaft 121 to rotate with the shaft and fixed face seal 140b attached to the aft cover 111 of pump housing 110. Each face seal interfaces with each other along a flat, precision polished surface to form a seal that prevents passage of any blood flow therebetween. Each face seal can be integral with the component with which it is attached, or more typically, is a separate component formed of a high wear material that is secured to the corresponding component. Typically, rotary seal 140 is preloaded such that there is a minimum contact force between face seals 140a, 140b to ensure a suitable sealing between interfacing surfaces for use with the variable pressure and flowrates within the blood flow passage of the pump. In this embodiment, the preload force is provided by a compliance member 141 that exerts a force when the pump is assembled to increase contact forces between seal faces. Here, compliance member 141 is defined as a thin wall, ridge or membrane that extends inwardly towards the rotor shaft. The fixed face seal is disposed against the compliance member such that compliance member 141 presses fixed face seal 140b against rotating face seal 140a during operation of the pump. It is appreciated that the dimensions and material properties of compliance member 141 can be defined to provide a desired preload in order to provide a suitable sealing contact force between seal faces as needed for a particular application. In some embodiments, compliance member 141 can be formed from aft cover 111 of pump housing, such as by precision machining.

In this embodiment, mechanical bearing assembly 130 includes two radial bearings stacked on the proximal portion of the rotor 120. Rotor 120 includes permanent drive magnets 150 to facilitate being rotationally driven by a motor stator 151 having electrically conductive coils. The coils are placed within an enclosure which surrounds the blood flow path and the rotor 120 disposed within pump housing 110. The motor stator 151 serves to rotate rotor 120 by the conventional application of electric power to the coils to drive the permanent drive magnets 150 incorporated into rotor 120. Elastomeric O-rings 153 keep the magnets from rotating in the rotor. Such magnets are selected for magnetic properties, length, and cross-sectional area in order to provide good electromagnetic coupling with the magnetic forces created by the motor stator 151. In some embodiments, the motor is a three phase, brushless DC motor. In other embodiments, the motor can be a toroidal, three phase or wye connected design. The stator may have a back iron design which is consistent with a typical radial flux gap motor. If desired, motor stator 151 can be incorporated within a separate, hermetically sealed enclosure that slides over pump housing into position. In some embodiments, the body of rotor 120 includes a magnetically hard ferromagnetic material, i.e., a material which forms a strong permanent magnet and which is resistant to demagnetization. The material of rotor body 120 is typically selected to be biocompatible and substantially non-thrombogenic. Rotor 120 can be formed as a unitary component or can be formed of separate components joined together. In some embodiments, the rotor body is formed as a unitary mass of a suitable material, such as an alloy of platinum, titanium, and cobalt. In other embodiments, the rotor body may be formed from a magnetic metal such as an iron-nickel alloy with an exterior coating of another material to increase the body's biocompatibility. Further details regarding suitable rotor designs are described in U.S. Pat. No. 5,588,812; 62/084, 946; 2016/0144089; 2014/0324165; and U.S. Pat. No. 9,265,870; each of which is incorporated herein by reference in its entirely for all purposes.

Figure 5:
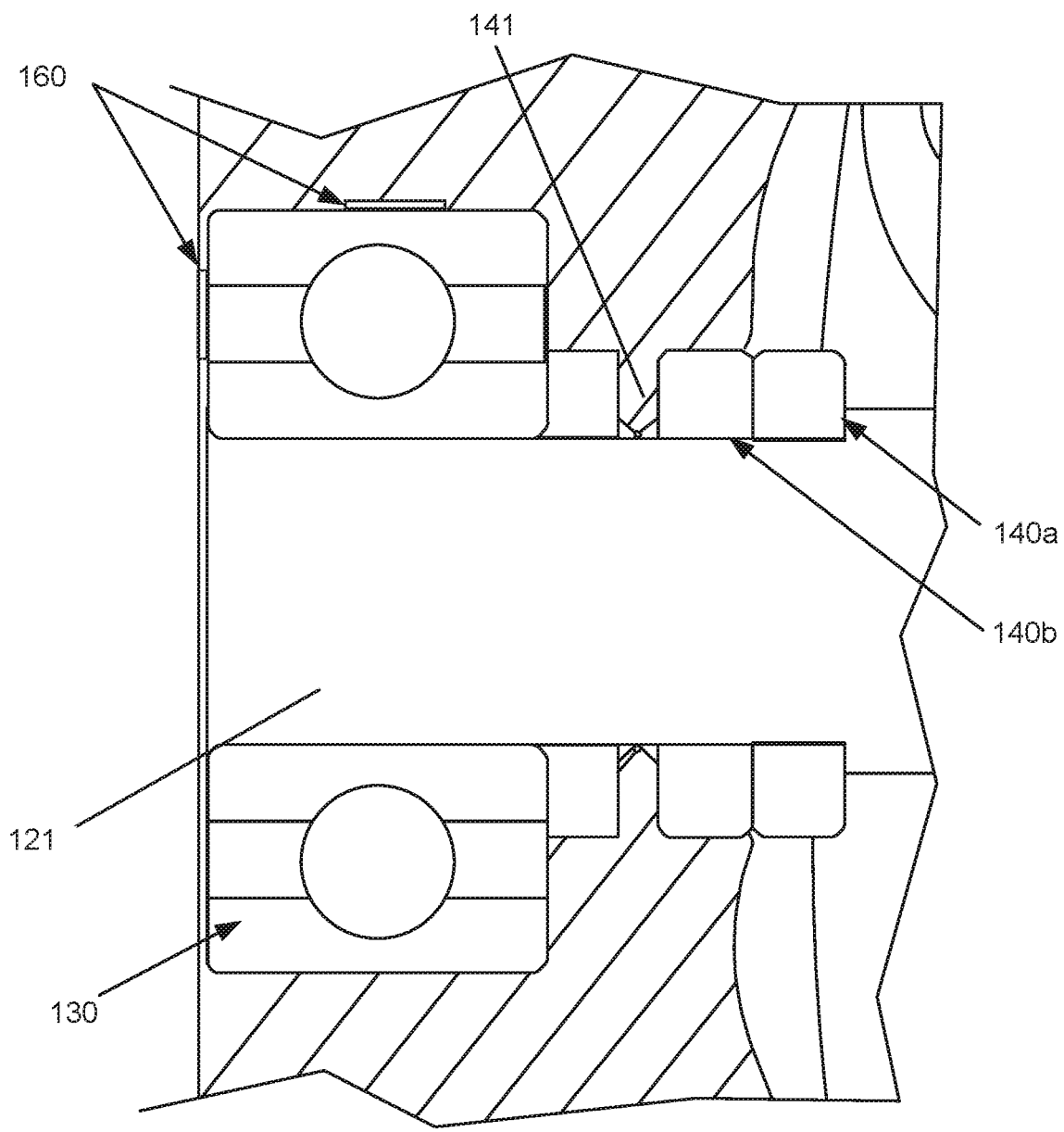
FIG. 5 shows a detailed view of a rotary seal and bearing assembly with monitoring sensors for use with a cantilevered rotor in accordance with some embodiments.

FIG. 5 shows a detail cross-sectional view of the bearing assembly 130 and rotary seal 140 of FIG. 4. As can be seen, a pair of sensors 160 are disposed within the pump housing 110 alongside bearing assembly 130. One sensor 160 extends along a same direction along which the rotor extends and the other sensor 160 extends in a perpendicular direction to the rotor such that, in combination, the two sensors 160 obtain movement data in either direction. Such configurations can utilize single-axis accelerometers, which can generally be smaller in size than multi-axis accelerometers. Monitoring movement along at least two axes is particularly useful as movement of the rotor can result in cyclical movement in unpredictable directions that would be otherwise difficult to identify if measuring movement in only one direction.

Figure 6:
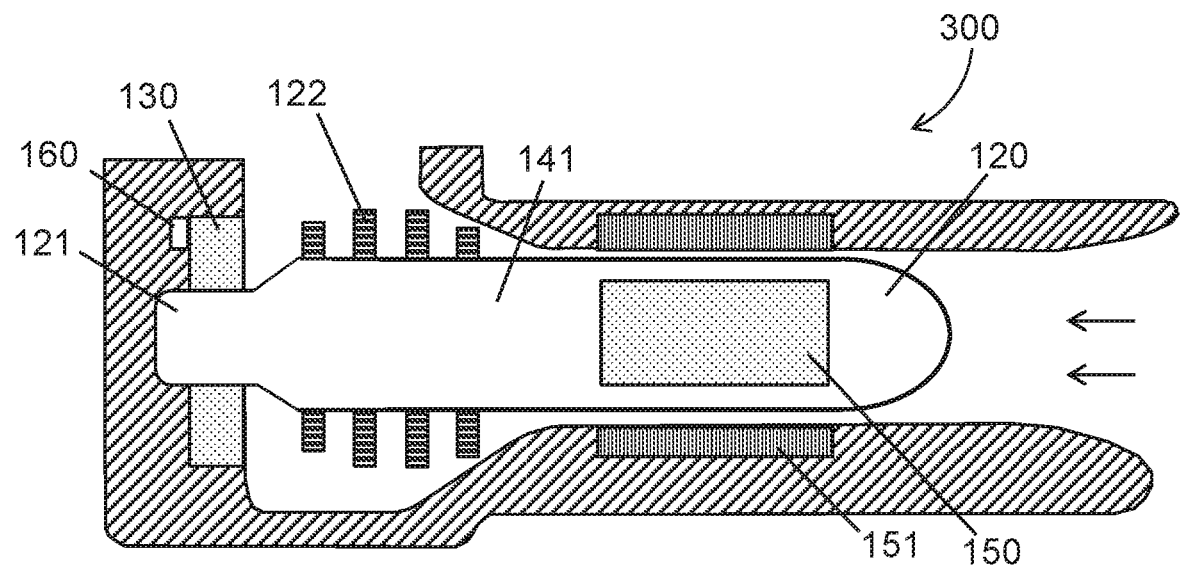
FIGS. 6-7 show alternative cantilever rotor designs having sensors for monitoring bearing and seal performance in accordance with some embodiments.
Figure 7:
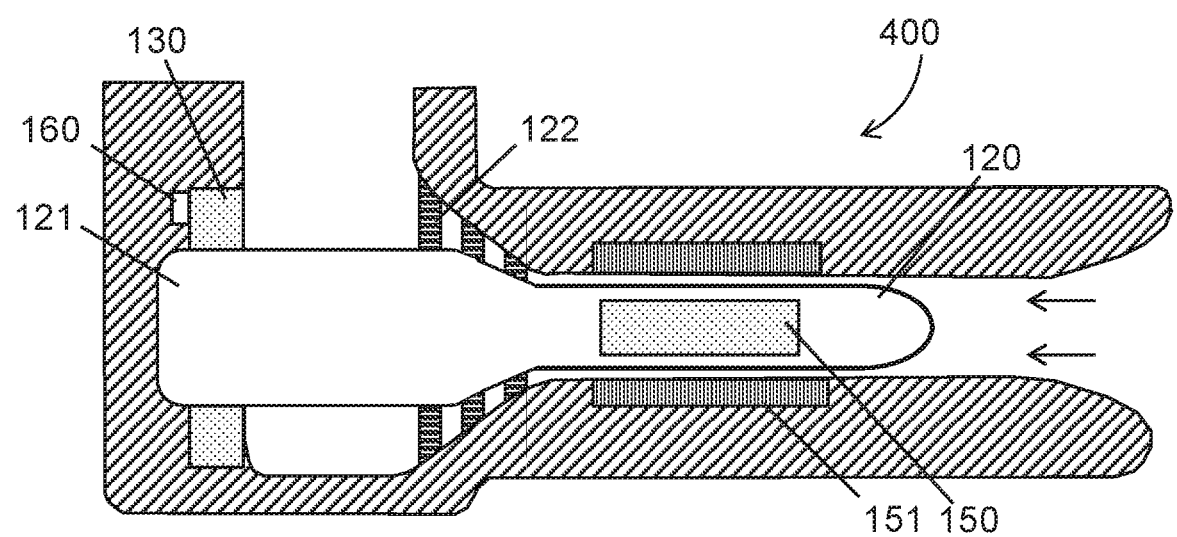

FIGS. 6-7 show alternative blood pump configurations for which monitoring of bearing and seal performance in accordance with aspects of the invention is particularly useful. Pump configurations 300, 400 have rotors 120 with rotor blades 122 that are moved towards the aft. This approach reduces the overall outside diameter of the motor stator 151, which allows for improved motor efficiency. Such configurations also minimize the gap between the outside diameter of rotor 120 and the inside diameter of the pump housing along the blood flow path such that it is particularly important that the bearing performance be maintained to prevent any lateral deviation of the rotor during operation of the pump. As in previous embodiments, one or more sensors 160 can be provided in the pump adjacent or near the bearing assembly 130 supporting the aft end of the rotor 120. In the embodiment of FIG. 7, the cantilever rotor 120 has rotor blades 122 shifted to the aft and having a substantially larger diameter at the aft end of the rotor. This configuration is advantageous for use with a cantilever design as any stresses and/or friction occurring within the bearing assembly during rotation are spread over a larger area. This may improve the durability and stability as well as extend the lifetime of the device.

Figure 8:
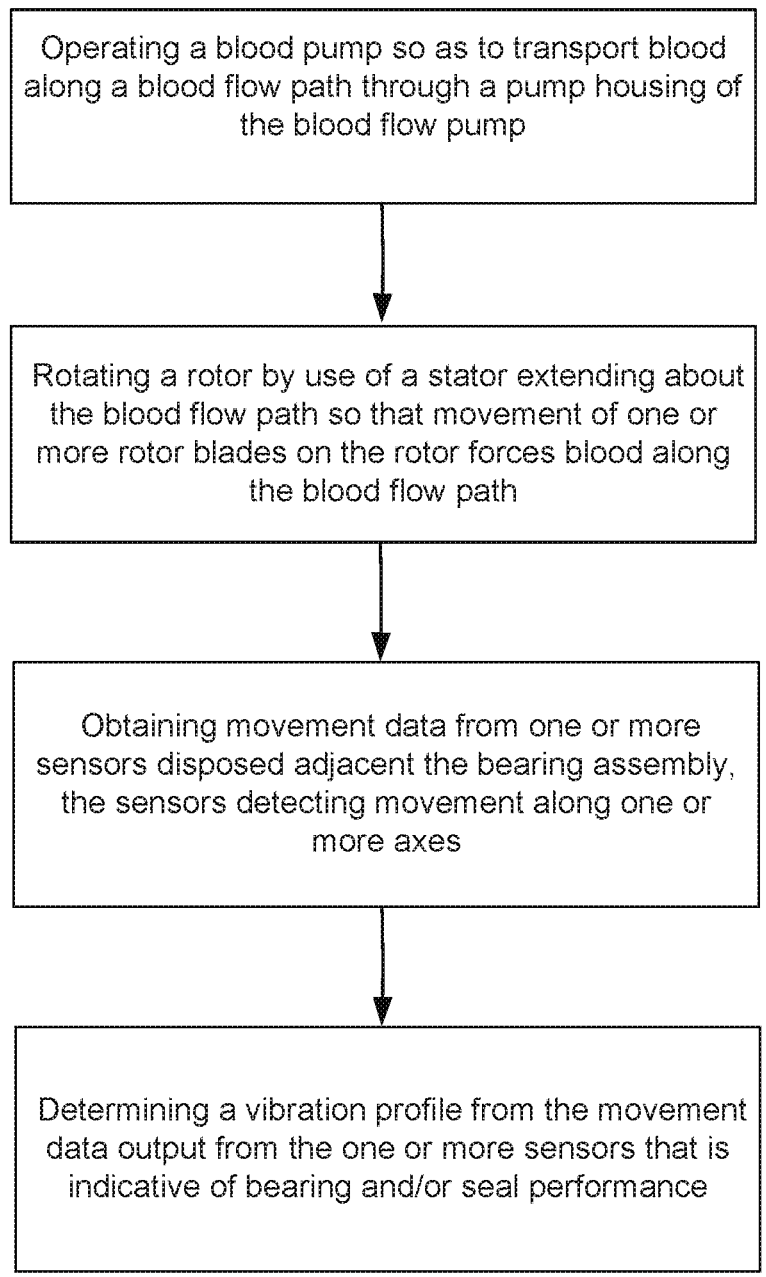
FIG. 8 shows a method of pumping blood with a blood pump in accordance with some embodiments.

FIG. 8 illustrates a method of monitoring performance of a bearing assembly and/or a rotary seal in a blood pump. Notably, this method can be used during manufacture or assembly of the device of during operation of the implanted device for diagnostic purposes. This method includes: operating a blood pump so as to transport blood along a blood flow path through a pump housing of the blood flow pump by rotating a rotor by use of a stator extending about the blood flow path so that movement of one or more rotor blades on the rotor forces blood along the blood flow path and monitoring a performance of the bearing assembly and/or rotary seal during operation of the pump with one or more sensors disposed adjacent the bearing assembly. The sensors are adapted to detect movement of the bearing assembly along one or more axes. Such sensors can be accelerometers or like sensors. The method can further include: determining a vibration profile from movement data output from the one or more sensors that is indicative of bearing and/or seal performance. This vibration profile can be compared to previously obtained vibration profiles and/or compared to a signature vibration profile that is a characteristic vibration profile of that pump design or a characteristic vibration profile that is unique to that particular pump, such as a vibration profile obtained during an initial calibration of the device before or after initial implantation of the blood pump.

In alternative embodiments, aspects of the invention described above may be used in centrifugal pumps. In centrifugal pumps, the rotors are shaped to accelerate the blood circumferentially and thereby cause blood to move toward the outer rim of the pump, whereas in the axial flow pumps, the rotors are more or less cylindrical with blades that are helical, causing the blood to be accelerated in the direction of the rotor's axis.

Figure 9:
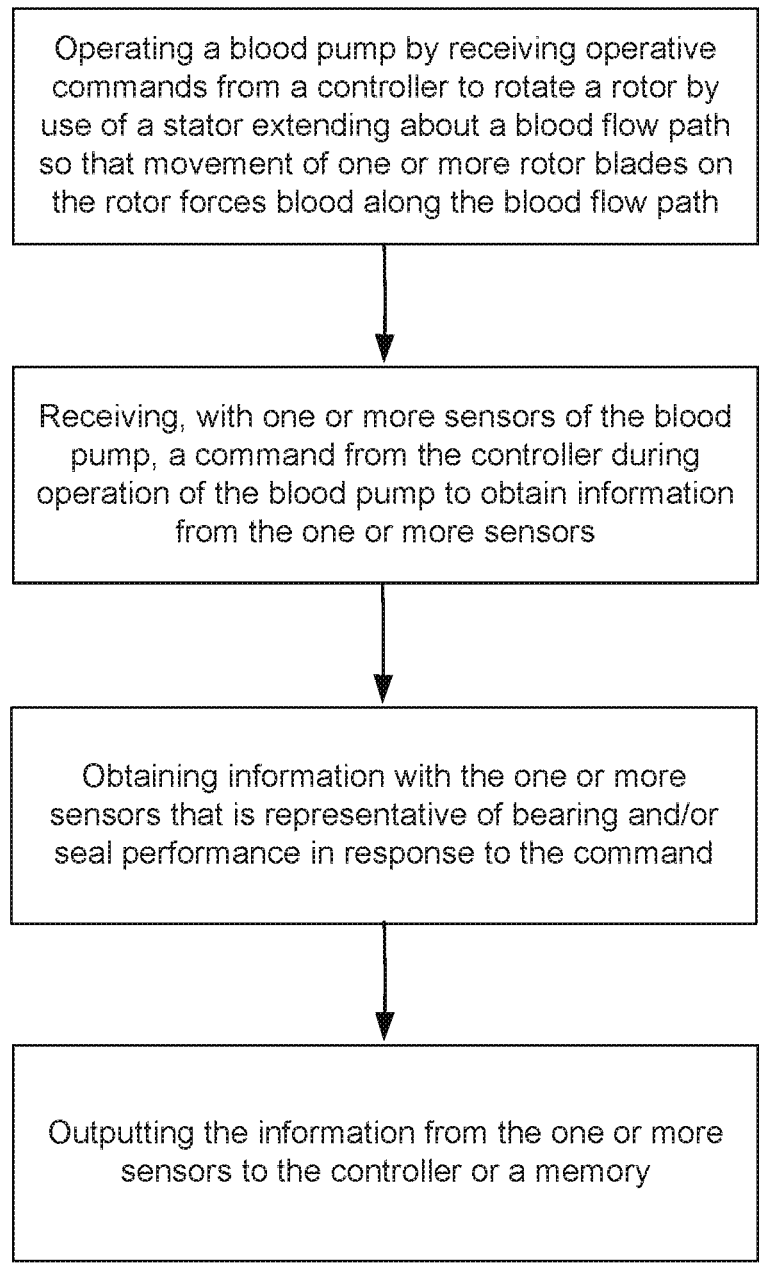
FIG. 9 shows a method of monitoring bearing and seal performance in a blood pump in accordance with some embodiments.

FIG. 9 illustrates a method of monitoring performance of a bearing assembly and/or a rotary seal in a blood pump. The method includes steps of: operating a blood pump by receiving operative commands from a controller to rotate a rotor by use of a stator extending about a blood flow path so that movement of one or more rotor blades on the rotor forces blood along the blood flow path; receiving, with one or more sensors of the blood pump, a command from the controller during operation of the blood pump to obtain information from one or more sensors; obtaining information with the one or more sensors that is representative of bearing and/or seal performance in response to the command; and outputting the information from the one or more sensors to the controller or a memory. In some embodiments, the one or more sensors are accelerometers and the information obtained is movement data for vibrational analysis. This method can be performed at pre-set intervals or can be performed in response to a detected condition and/or determined performance parameter based on the information received from the one or more sensors, or as needed. In some embodiments, the operative commands can be modified in response to the information received from the one or more sensors.

In the foregoing specification, the invention is described with reference to specific embodiments thereof, but those skilled in the art will recognize that the invention is not limited thereto. Various features and aspects of the above-described invention can be used individually or jointly. It is appreciated that any of the aspects or features of the embodiments described herein could be modified, combined or incorporated into any of the embodiments described herein, as well as in various other types and configurations of pumps. Further, the invention can be utilized in any number of environments and applications beyond those described herein without departing from the broader spirit and scope of the specification. The specification and drawings are, accordingly, to be regarded as illustrative rather than restrictive

What is claimed is:
1. An implantable blood pump comprising:
a pump housing defining a blood flow passage therethrough;
a rotor including a rotatable shaft that extends into the passage such that a distal portion of the rotor facilitates blood flow through the passage upon rotation of the rotatable shaft;
a mechanical bearing assembly coupled with a proximal portion of the rotatable shaft so as to allow rotation of the rotor during operation of the pump;
a seal disposed along the rotatable shaft between the bearing assembly and the blood flow passage, the seal being adapted to avoid contact between the bearing assembly and any blood flowing through the blood flow passage during operation of the pump; and
one or more sensors adapted to obtain information during operation of the pump that is representative of performance of the bearing assembly and/or the seal.

2. The blood pump of claim 1, wherein the one or more sensors are positioned and adapted to obtain movement data along one or more axes during operation of the pump over a period of time to allow monitoring of performance of the bearing assembly and/or seal from a vibration profile determined from the movement data.

3. The blood pump of claim 1, wherein the bearing assembly is a mechanical bearing assembly.

4. The blood pump of claim 1, wherein the information comprises one or both of movement of the bearing assembly and/or movement of the rotatable shaft.

5. The blood pump of claim 1, wherein the information comprises cyclical vibrational movement indicative of bearing performance.

6. The blood pump of claim 1, wherein the one or more sensors are accelerometers.

7. The blood pump of claim 1, wherein the one or more sensors include a multi-axis accelerometer.

8. The blood pump of claim 2, wherein the one or more sensors include at least a first and second accelerometers adapted and positioned to detect movement data along first and second axes, respectively.

9. The blood pump of claim 8, wherein the first and second axes are transverse to one another.

10. The blood pump of claim 1, wherein the one or more sensors include acoustic emission sensors.

11. The blood pump of claim 1, wherein the one or more sensors include any of:
optical detectors and proximity detectors.

12. The blood pump of claim 1, further comprising:
a memory communicatively coupled with the one or more sensors so as to store the information obtained from the one or more sensors.

13. The blood pump of claim 1, further comprising:
a controller communicatively coupled with the one or more sensors and configured to obtain movement data.

14. The blood pump of claim 13, wherein the controller is configured to obtain movement data from the one or more sensors upon receiving a command to obtain data.

15. The blood pump of claim 1, further comprising:
a processor coupled with a memory having readable programmable instructions recorded thereon, which are configured to:
determine a vibration profile from the movement data obtained from the one or more sensors, the vibration profile indicative of a performance of the bearing assembly and/or the seal.

16. The blood pump of claim 15, wherein the processor is further configured to:
compare the vibration profile with a previously obtained vibration profile and/or a signature profile characteristic of the pump or a type of the pump.

17. A method of monitoring bearing and/or seal performance in a blood pump, the method comprising:
- operating a blood pump so as to transport blood along a blood flow path through a pump housing of the blood flow pump, wherein operating the blood pump comprises rotating a rotatable shaft of the rotor so that movement of the rotor forces blood along the blood flow path, the rotor being rotatably supported by a bearing assembly that is sealed from blood flowing through the blood flow path by a rotary seal; and
- obtaining movement data from one or more sensors coupled with the pump, the movement data corresponding to movement of the bearing assembly along one or more axes during operation of the pump; and
- determining a vibration profile from the movement data from the one or more sensors that is indicative of a performance of the bearing assembly and/or the rotary seal.

18. The method of claim 17, wherein the one or more sensors are one or more accelerometers.

19. The method of claim 17, wherein the one or more sensors include a multi-axis accelerometer.

20. The method of claim 17, wherein the one or more sensors include at least a first and second accelerometer adapted and positioned to detect movement data along first and second axes, respectively, the first and second axes being transverse to one another.

21. The method of claim 17, wherein obtaining movement data comprises obtaining movement data wirelessly from the one or more sensors or from a memory coupled with the one or more sensors.

22. The method of claim 17, wherein obtaining movement data comprises obtaining movement data at regular intervals and/or upon receiving a command to obtain data.

23. The method of claim 17, further comprising:
- comparing the vibration profile with a previously obtained vibration profile and/or a signature profile characteristic of the pump or a type of the pump.

24. The method of claim 23, wherein the signature vibration profile is obtained during a calibration and/or at an initial implantation of the device.

* * * * *

UNITED STATES PATENT AND TRADEMARK OFFICE
CERTIFICATE OF CORRECTION

PATENT NO. : 10,660,998 B2  
APPLICATION NO. : 16/322403  
DATED : May 26, 2020  
INVENTOR(S) : William V. Hodges Page 1 of 1

It is certified that error appears in the above-identified patent and that said Letters Patent is hereby corrected as shown below:

On the Title Page

Item (73), Assignee name: "TCI LLC" should read --TC1 LLC--.

Signed and Sealed this  
Eleventh Day of August, 2020

Andrei Iancu  
*Director of the United States Patent and Trademark Office*